(12) United States Patent
McDaniel

(10) Patent No.: US 6,403,775 B1
(45) Date of Patent: Jun. 11, 2002

(54) ERYTHRONOLIDE COMPOUNDS

(75) Inventor: Robert McDaniel, Palo Alto, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/429,349

(22) Filed: Oct. 28, 1999

Related U.S. Application Data

(60) Provisional application No. 60/105,987, filed on Oct. 28, 1998.

(51) Int. Cl.[7] .................. C07H 17/08; C07D 321/00
(52) U.S. Cl. .................. 536/7.2; 549/200; 549/267
(58) Field of Search .................. 435/4; 514/29; 536/7.2; 549/200, 267

(56) References Cited

U.S. PATENT DOCUMENTS

| | | | |
|---|---|---|---|
| 4,551,433 A | 11/1985 | DeBoer | |
| 4,874,748 A | 10/1989 | Katz et al. | |
| 5,063,155 A | 11/1991 | Cox et al. | |
| 5,098,837 A | 3/1992 | Beckmann et al. | |
| 5,149,639 A | 9/1992 | Katz et al. | |
| 5,168,052 A | 12/1992 | Cox et | |
| 5,252,474 A | 10/1993 | Gewain et al. | |
| 5,514,544 A | 5/1996 | Rao et al. | |
| 5,824,513 A | 10/1998 | Katz et al. | 435/76 |
| 5,998,194 A | 12/1999 | Summers, Jr. et al. | 435/252.33 |
| 6,004,787 A | 12/1999 | Katz et al. | 435/183 |
| 6,200,813 B1 | 3/2001 | Katz et al. | 435/477 |
| 6,060,234 A1 * | 5/2001 | Katz et al. | 435/4 |
| 6,271,255 B1 | 8/2001 | Leadlay et al. | 514/450 |

FOREIGN PATENT DOCUMENTS

| | | |
|---|---|---|
| EP | 0 238 323 | 12/1994 |
| EP | 0 791 655 | 8/1997 |
| EP | 0 791 656 | 8/1997 |
| WO | WO 93/13663 | 1/1992 |
| WO | WO 95/08548 | 3/1995 |
| WO | WO 97/13845 | 10/1996 |
| WO | WO 96/40968 | 12/1996 |
| WO | WO 97/23630 | 12/1996 |
| WO | WO 97 02358 | 1/1997 |
| WO | WO 98/01546 | 1/1998 |
| WO | WO 98/01571 | 1/1998 |
| WO | WO 98 49315 | 11/1998 |
| WO | WO 98 51695 | 11/1998 |

OTHER PUBLICATIONS

Xue et al., PNAS USA (1999) 96:11740–11745.
Donadio, S. et al., Proc Natl Acad Sci USA (1993), 90:7119–7123.
Donadio, et al., Industrial Microorganism, Basic and Applied Molecular Genetics 91993, R.H. Baltz, G.D. Hegeman and P1L. Skatrud (eds) (Amer. Soc. Microbial).
Khosla, C. et al., Tibtech Sep. (1996) 14:335–341.
Marsden, A.F.A. et al., Science (1998), 279:199–202.
Perun, T.J., Drug Action and Drug Resistance in Bacteria, vol. 1, S. Mitsuhashi (ed) Univ. Park Press, Baltimore, 1977.
Jacobsen J.R. et al. (1998). *J Am Chem Soc* 120(35):9096–9097.
Kaiho T. et al. (1982). *J Org Chem* 47:1612–1614.
Khosla C. (1997). *Chem Reviews* 97(7):2577–2590.
Liu L. et al. (1997). *J Am Chem Soc* 119(43):10553–10554.
McDaniel R. et al. (1999). *Proc Natl Acad Sci USA* 96(5):1846–1851.
Ruan X. et al. (1997). J Bacteriol 179(20):6416–6425.

* cited by examiner

Primary Examiner—Padmashri Ponnaluri
(74) Attorney, Agent, or Firm—Kevin Kaster; Brenda J. Wallach

(57) ABSTRACT

Genetic engineering of the erythromycin polyketide synthase genes to effect combinatorial alterations of catalytic activities in the biosynthetic pathway can be used to generate a library of macrolides impractical to produce by chemical methods. The library includes examples of analogs with one, two and three altered carbon centers of the polyketide products.

4 Claims, 4 Drawing Sheets

SEQUENCE LISTING

<160> NUMBER OF SEQ ID NOS: 21

<210> SEQ ID NO 1
<211> LENGTH: 26
<212> TYPE: DNA
<213> ORGANISM: Artificial Sequence
<220> FEATURE:
<223> OTHER INFORMATION: module 1 BamHI -continued

```
<400> SEQUENCE: 1
ggcgcagcag ggatccgtct cgtct                                        26

<210> SEQ ID NO 2
<211> LENGTH: 26
<212> TYPE: DNA
<213> ORGANISM: Artificial Sequence
<220> FEATURE:
<223> OTHER INFORMATION: module 1 RstI

<400> SEQUENCE: 2
gcgcgtctgg ctgcagccga agccgg                                       26

<210> SEQ ID NO 3
<211> LENGTH: 26
<212> TYPE: DNA
<213> ORGANISM: Artificial Sequence
<220> FEATURE:
<223> OTHER INFORMATION: module 1XbaI

<400> SEQUENCE: 3
gccggccgaa tctagagtgg gcgcgc                                       26

<210> SEQ ID NO 4
<211> LENGTH: 24
<212> TYPE: DNA
<213> ORGANISM: Artificial Sequence
<220> FEATURE:
<223> OTHER INFORMATION: module 2 BamHI

<400> SEQUENCE: 4
tccgacggtg gatccgtgtt cgtc                                         24

<210> SEQ ID NO 5
<211> LENGTH: 24
<212> TYPE: DNA
<213> ORGANISM: Artificial Sequence
<220> FEATURE:
<223> OTHER INFORMATION: module 3 BamHI

<400> SEQUENCE: 5
tccgacggtg gatccgtgtt cgtc                                         24

<210> SEQ ID NO 6
<211> LENGTH: 26
<212> TYPE: DNA
<213> ORGANISM: Artificial Sequence
<220> FEATURE:
<223> OTHER INFORMATION: module 3 PstI

<400> SEQUENCE: 6
gcgctactgg ctgcagcccg ccgcac                                       26

<210> SEQ ID NO 7
<211> LENGTH: 26
<212> TYPE: DNA
<213> ORGANISM: Artificial Sequence
<220> FEATURE:
<223> OTHER INFORMATION: module 3 XbaI

<400> SEQUENCE: 7
gaccggcgag tctagacaac ggctcg                                       26

<210> SEQ ID NO 8
<211> LENGTH: 26
```

```
<212> TYPE: DNA
<213> ORGANISM: Artificial Sequence
<220> FEATURE:
<223> OTHER INFORMATION: module 4 BamHI

<400> SEQUENCE: 8
cgcgccgcgc ggatccgtcc tggtct                                    26

<210> SEQ ID NO 9
<211> LENGTH: 26
<212> TYPE: DNA
<213> ORGANISM: Artificial Sequence
<220> FEATURE:
<223> OTHER INFORMATION: module 4 PstI

<400> SEQUENCE: 9
gcgcttctgg ctgcagccgc accggc                                    26

<210> SEQ ID NO 10
<211> LENGTH: 26
<212> TYPE: DNA
<213> ORGANISM: Artificial Sequence
<220> FEATURE:
<223> OTHER INFORMATION: module 4 XbaI

<400> SEQUENCE: 10
agggccgaac tctagagacc ggctcg                                    26

<210> SEQ ID NO 11
<211> LENGTH: 24
<212> TYPE: DNA
<213> ORGANISM: Artificial Sequence
<220> FEATURE:
<223> OTHER INFORMATION: module 5 BamHI

<400> SEQUENCE: 11
actcgccgcg gatccgcgat ggtg                                      24

<210> SEQ ID NO 12
<211> LENGTH: 24
<212> TYPE: DNA
<213> ORGANISM: Artificial Sequence
<220> FEATURE:
<223> OTHER INFORMATION: module 5 PstI

<400> SEQUENCE: 12
cggtactggc tgcagatccc cacc                                      24

<210> SEQ ID NO 13
<211> LENGTH: 24
<212> TYPE: DNA
<213> ORGANISM: Artificial Sequence
<220> FEATURE:
<223> OTHER INFORMATION: module 5 XbaI

<400> SEQUENCE: 13
gaggagggct ctagactcgc ccag                                      24

<210> SEQ ID NO 14
<211> LENGTH: 24
<212> TYPE: DNA
<213> ORGANISM: Artificial Sequence
<220> FEATURE:
<223> OTHER INFORMATION: module 6 BamHI

<400> SEQUENCE: 14
```

```
tccgccggcg gattcgtttt cgtc                                          24

<210> SEQ ID NO 15
<211> LENGTH: 24
<212> TYPE: DNA
<213> ORGANISM: Artificial Sequence
<220> FEATURE:
<223> OTHER INFORMATION: module 6 PstI

<400> SEQUENCE: 15
cggtactggc tgcagccgga ggtg                                          24

<210> SEQ ID NO 16
<211> LENGTH: 24
<212> TYPE: DNA
<213> ORGANISM: Artificial Sequence
<220> FEATURE:
<223> OTHER INFORMATION: module 6 XbaI

<400> SEQUENCE: 16
gtgggggcct ctagagcggt gcag                                          24

<210> SEQ ID NO 17
<211> LENGTH: 26
<212> TYPE: DNA
<213> ORGANISM: Artificial Sequence
<220> FEATURE:
<223> OTHER INFORMATION: SpeI site of the AC P2 domain

<400> SEQUENCE: 17
cggtttcctc actagtgagc tcggca                                        26

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
tttggatccg tgttcgtctt cccgggtcag gggtcg                             36

<210> SEQ ID NO 19
<211> LENGTH: 36
<212> TYPE: DNA
<213> ORGANISM: Artificial Sequence
<220> FEATURE:
<223> OTHER INFORMATION: Primer

<400> SEQUENCE: 19
tttctgcagc cagtaccgct ggtgctggaa ggcgta                             36

<210> SEQ ID NO 20
<211> LENGTH: 53
<212> TYPE: DNA
<213> ORGANISM: Artificial Sequence
<220> FEATURE:
<223> OTHER INFORMATION: AT/ACP linker

<400> SEQUENCE: 20
ccggtgcggc tcgacggaga attcgcgcat catcatcatc atcattaact g ca         53

<210> SEQ ID NO 21
<211> LENGTH: 45
<212> TYPE: DNA
<213> ORGANISM: Artificial Sequence
```

```
<220> FEATURE:
<223> OTHER INFORMATION: AT/ACP linker

<400> SEQUENCE: 21
gttaatgatg atgatgatga tgcgcgaatt ctccgtcgag ccgca          45
```

ERYTHRONOLIDE COMPOUNDS

CROSS-REFERENCE TO RELATED APPLICATIONS

This application claims priority to U.S. provisional Application Serial No. 60/105,987, filed Oct. 28, 1998, now lapsed. Each of the above patent applications is incorporated herein by reference.

REFERENCE TO GOVERNMENT FUNDING

This invention was supported in part by SBIR grant 1R43-CA75792-01. The U.S. government has certain rights in this invention.

This application is related to U.S. Ser. No. 09/073,538, filed May 6, 1998, which is a continuation-in-part of U.S. Ser. No. 08/846,247, filed Apr. 30, 1997, and is related to PCT application No. U.S. Ser. No. 98/08792 and U.S. provisional application Serial No. 60/076,919, filed Mar. 5, 1998, now lapsed.

FIELD OF THE INVENTION

The present invention provides recombinant DNA compounds and host cells containing novel polyketide synthase (PKS) genes and novel polyketides. The invention relates to the fields of chemistry, medicinal chemistry, human and veterinary medicine, molecular biology, pharmacology, agriculture, and animal husbandry.

BACKGROUND OF THE INVENTION

Few molecules have captured interest in both chemotherapy and chemistry to the extent of the polyketide erythromycin and its semi-synthetic derivatives. Erythromycin and its congeners are the third most widely used class of antibiotics, with current worldwide sales exceeding US $3.5 billion. In addition, erythromycin analogs are gaining interest for their potential use in the treatment of gastrointestinal disorders (Omura, "The expanded horizon for microbial metabolites—a review," *Gene* 115, 141–149 (1992)), inflammatory diseases (Kawasaki et al., "Roxithromycin inhibits cytokine production by and neutrophil attachment to human bronchial epithelial cells in vitro," *Antimicrob. Agents Chemother.* 42, 1499–1502 (1998)), and as next-generation antibiotics for treatment of emerging drug-resistant strains of bacteria (Agoudiras et al., "In-vitro antibacterial activity of RU 004 (HMR 3004), a novel ketolide derivative active against respiratory pathogens," *Antimicrob. Agents Chemother.* 41, 2149–2158 (1997)).

The chemical challenges of erythromycin attracted the talents of R. B. Woodward and 48 colleagues who described its complete synthesis in a series of landmark publications (Woodward et al., "Asymmetric total synthesis of erythromycin. 1. Synthesis of erythronolide A secoacid derivative via asymmetric induction;" 2. Synthesis of an erythronolide A lactone system;" and 3. Total synthesis of erythromycin," *J. Am. Chem. Soc.* 103, 3210–3217 (1981)), and of a cadre of medicinal chemists who prepared analogs leading to the important second generation of macrolide antibiotics—clarithromycin, azithromycin, and others (Chu, "Recent developments in 14- and 15-membered macrolides," *Exp. Opin. Invest. Drugs* 4, 65–94 (1995)). Although such efforts effectively saturated the chemical modifications possible at the existing functional groups of the macrolide ring, most of the ring remained inert to chemical modification.

The modular nature of polyketide biosynthesis (Cortés et al., "An unusually large multifunctional polypeptide in the erythromycin-producing polyketide synthase of Saccharopolyspora erythraea," *Nature* 348, 176–178 (1990); and Donadio et al., "Modular organization of genes required for complex polyketide biosynthesis," *Science* 252, 675–679 (1991)) has facilitated genetic engineering strategies for the production of novel polyketides (McDaniel et al., "Rational design of aromatic polyketide natural products by recombinant assembly of enzymatic subunits," *Nature* 375, 549–554 (1995) and Katz, "Manipulation of modular polyketide synthases," *Chem. Rev.* 97, 2557–2576 (1997)).

The "modular" PKSs are each encoded by a cluster of contiguous genes and have a linear, modular organization of similar catalytic domains that both build and modify the polyketide backbone. Each module contains a set of three domains—a ketosynthase (KS), an acyltransferase (AT), and an acyl carrier protein (ACP)—that catalyze a 2-carbon extension of the growing polyketide chain (FIG. 1 and O'Hagan, The polyketide metabolites (E. Horwood, New York, 1991)). The choice of extender unit used by each module—acetate, propionate, or other small organic acids in the form of CoA thioesters—is determined by the specificity of the AT domain (Oliynyk et al., "A hybrid modular polyketide synthase obtained by domain swapping," *Chem. & Biol.* 3, 833–839 (1996); Liu et al., "Biosynthesis of 2-nor-6-deoxyerythronolide B by rationally designed domain substitution," *J. Am. Chem. Soc.* 119, 10553–10554 (1997); and Ruan et al., "Acyltransferase domain substitutions in erythromycin polyketide synthase yields novel erythromycin derivatives," *J. Bacteriol.* 179, 6416–6425 (1997)).

With each 2-carbon chain extension, the oxidation state of the β-carbon is embedded as a ketone, hydroxyl, methenyl, or methylene group by the presence or absence of one, two, or three additional catalytic domains in the module—a ketoreductase (KR), dehydratase (DH) and/or enoyl reductase (ER). In effect, the composition of catalytic domains within a module provides a "code" for the structure of each 2-carbon unit, and the order of modules codes for the sequence of the 2-carbon units, together creating a linear template for the linear polyketide product. The remarkable structural diversity of polyketides is governed by the combinatorial possibilities of arranging catalytic domains within each module, the sequence and number of modules, and the post-polyketide synthesis cyclization and "tailoring enzymes" that accompany the PKS genes. The direct correspondence between the catalytic domains of modules in a PKS and the structure of the resulting biosynthetic product portends the possibility of modifying polyketide structure by modifying the domains of the modular PKS.

There remains a need for compounds with modifications of the chemically inert sites of polyketides such as erythromycin that can be produced by genetic engineering. Such novel macrolides could in themselves provide the basis for new pharmaceuticals or serve as scaffolds for new semi-synthetic analogs. The present invention meets this need.

SUMMARY OF THE INVENTION

The present invention provides a library of recombinant PKS genes, host cells containing those genes, and the polyketides produced by those host cells. The polyketides provided by the invention include the polyketides shown in FIG. 2, as well as the polyketides that can be prepared by any of the myriad possible combinations of the recombinant PKS genes of the invention.

The present invention also provides the glycosylated and hydroxylated forms of the polyketides of the invention that can be produced by contacting the polyketides described herein with host cells selected from the group consisting of *Saccharopolyspora erythraea, Streptomyces venezuelae, S. narbonensis, S. antibioticus, S. fradiae, S. thernotolerans*, and *Micromonospora megalomicea*. The invention also provides compounds derived from the foregoing by chemical modification, including the C-6 to C-9 hemiketals formed from the compounds of the invention having a C-6 hydroxyl group and a C-9 keto group by treatment with mild acid.

The present invention also provides novel polyketides in isolated and purified form, as well as in cultures of recombinant host cells. Particular polyketides provided include 5,6-dideoxy-10-norerythronolide B, 6-deoxy-12-norerythronolide B, 2, 10-bisnor-3-oxo-6-deoxy-10,11-anhydroerythronolide B, and 2,4-bisnor-3-oxo-6-deoxyerythronolide B, as well as the glycosylated and hydroxylated forms thereof The present invention also provides the polyketide compounds of the invention in the form of pharmaceutical compositions, and methods for using the same in the treatment of disease.

These and other embodiments, modes, and aspects of the invention are described in more detail in the following description, the examples, and claims set forth below.

DETAILED DESCRIPTION OF THE INVENTION

The present invention provides a combinatorial library of novel polyketides produced by novel genetically engineered proteins related to deoxyerythronolide B synthase (DEBS), the PKS that produces the macrolide ring of erythromycin. The library was constructed by substituting the ATs and β-carbon processing domains of DEBS with counterparts from the rapamycin PKS (RAPS; Schwecke et al., "The biosynthetic gene cluster for the polyketide immunosuppressant rapamycin," *Proc. Natl. Acad. Sci., U.S.A.* 92, 7839–7843 (1995)) that encode alternative substrate specificities and β-carbon reduction/dehydration activities. Engineered DEBS containing single, double, and triple catalytic domain substitutions catalyzed production of novel erythromycin macrolactones with corresponding single, double, and triple modifications. The ability to manipulate multiple catalytic centers of the PKS simultaneously demonstrates the robustness of the engineering process and the potential for creating libraries of novel polyketides that are impractical to prepare in the chemistry laboratory.

Figure 1:
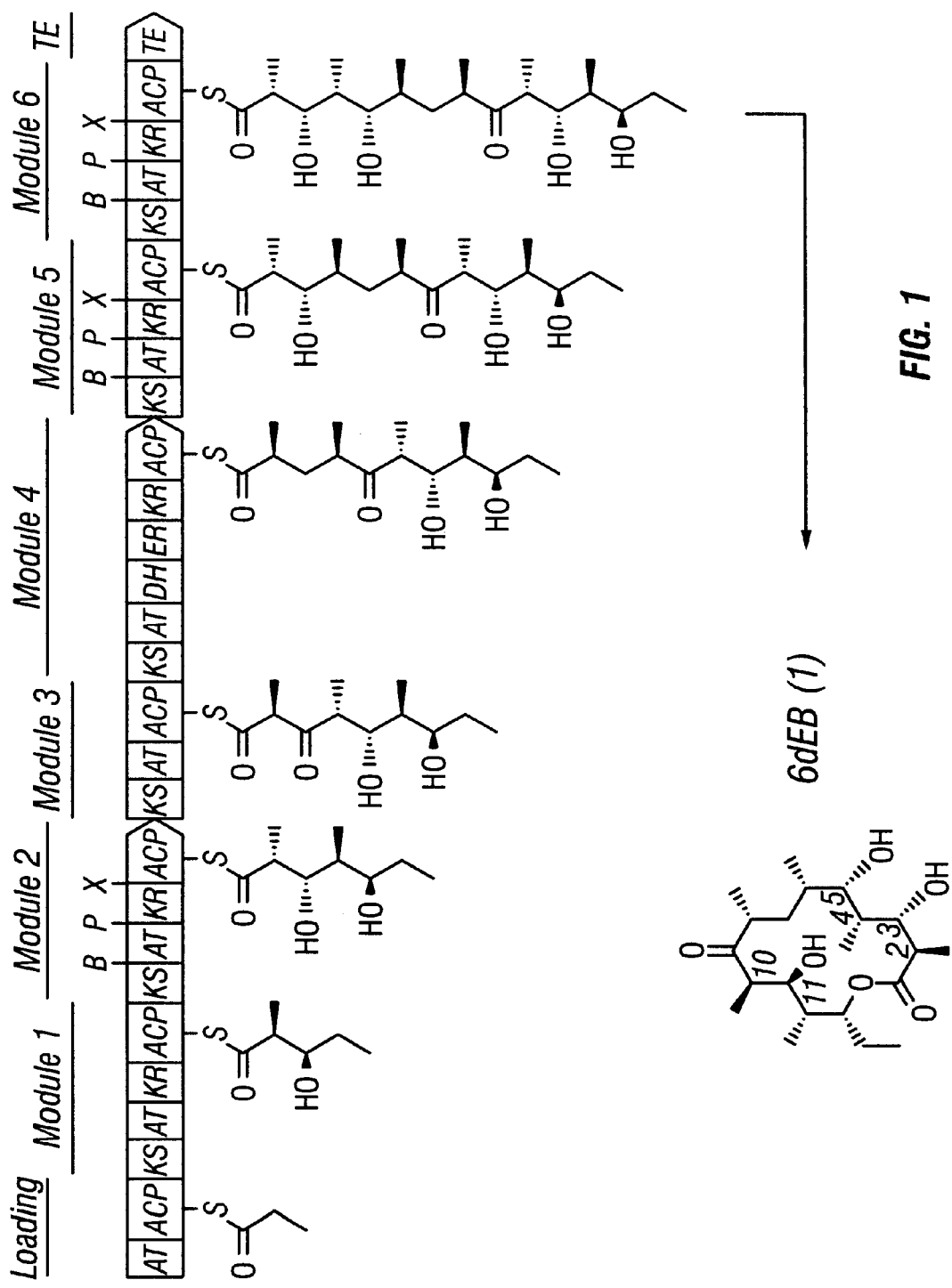
FIG. 1 shows the genetic architecture of 6-deoxyerythronolide B synthase (DEBS). Each module catalyses one cycle of chain extension and associated β-keto modification. DEBS catalyzes formation of 6-deoxyerythronolide B (1) from decarboxylative condensations between one propionyl CoA priming unit and six methylmalonyl CoA extender units. For β-carbon processing, modules 1, 2, 5, and 6 contain ketoreductase (KR) domains, module 4 contains the complete KR, dehydratase (DH), and enoyl reductase (ER) domain set, and module 3 lacks any functional β-carbon modifying domains. The loading segment consists of priming AT and ACP domains, and a thioesterase (TE) catalyzes the release and cyclization of the polyketide chain. To construct the recombinant genes described, restriction endonuclease sites were engineered around AT and KR domains in modules 2, 5, and 6 (B, BamHI; P, PstI; X, XbaI).

The DEBS multienzyme complex consists of three large subunits (>300 kDa), each containing 2 modules (FIG. 1). In all, there are 28 catalytic domains responsible for the priming, chain extension, β-carbon modification, and cyclization of the polyketide during biosynthesis of 6-deoxyerythronolide B (6-dEB, 1; Cortés et al., "An unusually large multifunctional polypeptide in the erythromycin-producing polyketide synthase of *Saccharopolyspora erythraea*," *Nature* 348, 176–178 (1990) and Donadio et al., "Modular organization of genes required for complex polyketide biosynthesis," *Science* 252, 675–679 (1991)).

Thus far, individual mutagenesis strategies that have successfully altered the catalytic properties of DEBS include:

i) deletion of modules to control chain length (Kao et al., "Engineered biosynthesis of a triketide lactone from an incomplete modular polyketide synthase," *J. Am. Chem. Soc.* 116, 11612–11613 (1994); Cortés et al., "Repositioning of a domain in a modular polyketide synthase to promote specific chain cleavage," *Science* 268, 1487–1489 (1995); Kao et al., "Manipulation of macrolide ring size by directed mutagenesis of a modular polyketide synthase," *J. Am. Chem. Soc.* 117, 9105–9106 (1995); and Kao et al., "Engineered biosynthesis of structurally diverse tetraketides by a trimodular polyketide synthase," *J. Am. Chem. Soc.* 118, 9184–9185 (1996));

ii) inactivation of reduction/dehydration domains to bypass β-carbon processing steps (Donadio et al., "Modular organization of genes required for complex polyketide biosynthesis," *Science* 252, 675–679 (1991); Donadio et al., "An erythromycin analog produced by reprogramming of polyketide synthesis," *Proc. Natl. Acad. Sci. U.S.A.* 90, 7119–7123 (1993); and Bedford et al., "A functional chimeric modular polyketide synthase generated via domain replacement," *Chem. & Biol.* 3, 827–831 (1996));

iii) substitution of AT domains to alter starter and extender unit incorporation (Oliynyk et al., "A hybrid modular polyketide synthase obtained by domain swapping," *Chem. & Biol.* 3, 833–839 (1996); Liu et al., "Biosynthesis of 2-nor-6-deoxyerythronolide B by rationally designed domain substitution," *J. Am. Chem. Soc.* 119, 10553–10554 (1997); Ruan et al., "Acyltransferase domain substitutions in erythromycin polyketide synthase yields novel erythromycin derivatives," *J Bacteriol.* 179, 6416–6425 (1997); Marsden et al., "Engineering broader specificity into an antibiotic-producing polyketide synthase," *Science* 279, 199–202 (1998); and Stassi et al., "Ethyl-substituted erythromycin derivatives produced by directed metabolic engineering," *Proc. Natl. Acad. Sci. USA* 95, 7305–7309 (1998));

iv) addition of reduction/dehydration domains to introduce catalytic activities (McDaniel et al., "Gain-of-function mutagenesis of a modular polyketide synthase" *J. Am. Chem. Soc.* 119, 4309–4310 (1997) and Kao et al., "Gain of function mutagenesis of the erythromycin polyketide synthase. 2. Engineered biosynthesis of an eight-membered ring tetraketide lactone," *J. Am. Chem. Soc.* 119, 11339–11340 (1997)); and v) substitution of ketoreductase (KR) domains to control hydroxyl stereochemistry (Kao et al., "Alcohol stereochemistry in polyketide backbones is controlled by the β-ketoreductase domains of modular polyketide synthases," *J Am. Chem. Soc.* 120, 2478–2479 (1998))

Although these experiments revealed some tolerance of DEBS for alteration of individual activities, the extent of this tolerance dictates the utility of the approach for producing large numbers of polyketides, which requires the enzyme's acceptance of multiple changes in the biosynthetic pathway.

The present invention illustrates the nature and size of libraries that can be expected from the combinatorial manipulation of modular PKSs.

The present invention provides systematically engineered single and multiple enzymatic domain substitutions in DEBS and demonstrates the broader applicability of PKS mutagenesis techniques. Modules 2, 5, and 6 of DEBS possess only a KR for β-carbon processing, and provide an excellent template for systematically testing the effects of AT specificity alteration, reductive domain deletion, and reductive domain gain-of-function on three different, albeit similar, modules.

For AT substitutions, the malonyl CoA transferase from module 2 of RAPS (rapAT2) was used to replace AT domains of DEBS. The resulting mutants were expected to incorporate acetate rather than propionate units to generate 6-dEB analogs lacking a methyl substituent at the engineered positions (Oliynyk et al., "A hybrid modular polyketide synthase obtained by domain swapping," *Chem. & Biol.* 3, 833–839 (1996) and Liu et al., "Biosynthesis of 2-nor-6-deoxyerythronolide B by rationally designed domain substitution," *J. Am. Chem. Soc.* 119, 10553–10554 (1997)).

Gain-of-function mutagenesis was performed by replacement of ketoreductases with cassettes containing the DH+KR domains from RAPS module 4 (rapDH/KR4) and the DH+ER+KR domains from RAPS module 1 (rapDH/ER/KR1). Successful substitution with these cassettes replaces the corresponding hydroxyl moieties of 6-dEB with alkene and alkane carbons, respectively (McDaniel et al., "Gain-of-function mutagenesis of a modular polyketide synthase," *J. Am. Chem. Soc.* 119, 4309–4310 (1997) and Kao et al., "Gain of function mutagenesis of the erythromycin polyketide synthase. 2. Engineered biosynthesis of an eight-membered ring tetraketide lactone," *J Am. Chem. Soc.* 119, 11339–11340 (1997)). Deletion mutagenesis to convert hydroxyl groups of 6-dEB to ketones was performed by substituting KR domains with a synthetic 18 amino acid fragment (AT/ACP linker) joining the AT and ACP domains.

Restriction sites were engineered around the boundaries of the AT and KR domains to facilitate mutagenesis (FIG. 1). The engineered sites had no effect on the level of 6-dEB production. Appropriate cassettes from RAPS were then inserted into the AT or KR positions of modules 2, 5, and 6 of the full DEBS system encoded on the Streptomyces expression plasmid pCK7 (Kao et al., "Engineered biosynthesis of a complete macrolactone in a heterologous host," *Science* 265, 509–512 (1994) and U.S. Pat. No. 5,672,491). The resulting plasmids were introduced into either *Streptomyces coelicolor* CH999 (McDaniel et al., "Engineered biosynthesis of novel polyketides," *Science* 262, 1546–1557 (1993) and U.S. Pat. No. 5,672,491) or *Streptomyces lividans* K4-114 (Ziernann and Betlach, January. 99, BioTechniques 26:106–110) and the transformed strains analyzed for polyketide production by LC/MS.

Nearly all of the strains expressing PKSs with a single mutation produced polyketides with molecular weights matching the predicted 6-dEB analog, and with production levels ranging from 1 to 70 percent of wild-type 6-dEB (1), as shown in Table 1, below.

TABLE 1

Polyketides produced by AT and KR Substitutions in DEBS modules 2, 5, and 6

| | Mutation | 6-dEB Analog Product | Cmpd # | Relative Yield |
|---|---|---|---|---|
| Module 2 | rapAT2 AT/ACP linker | 10-desmethyl NP | 2 | 0.2 |
| | rapDH/KR4 | 10,11-anhydro | 3 | 0.02 |
| | rapDH/ER/KR1 | 11-deoxy | 4 | 0.2 |
| Module 5 | rapAT2 | 4-desmethyl | 7 | 0.04 |
| | AT/ACP linker | 5-deoxy-5-oxo | 8 | 0.1 |
| | rapDH/KR4 | 4,5-anhydro | 9 | ND |
| | rapDH/ER/KR1 | 5-deoxy-5-oxo; 5-deoxy | 8, 10 | 0.5, 0.04 |
| Module 6 | rapAT2 | 2-desmethyl | 11 | 0.7 |
| | AT/ACP linker | 3-deoxy-3-oxo; 2-desmethyl-3-deoxy-3-oxo | 12, 14 | 0.3, 0.4 |
| | rapDH/KR4 | 2,3-anhydro | 13 | 0.4 |
| | rapDH/ER/KR1 | 3-deoxy-3-oxo; 2,3-anhydro | 12, 13 | 0.3, 0.2 |
| Module 2(AT + KR) | rapAT2 + AT/ACP linker | NP | | |
| | rapAT2 + rapDH/KR4 | 10-desmethyl-10,11-anhydro | 5 | <0.005 |
| | rapAT2 + rapDH/ER/KR1 | 10-desmethyl-11-deoxy | 6 | <0.005 |
| Module 6(AT + KR) | rapAT2 + AT/ACP linker | 2-desmethyl-3-deoxy-3-oxo | 14 | 0.2 |
| | rapAT2 + rapDH/KR4 | 2-desmethyl-(3-epi) | 15 | ND |
| | rapAT2 + rapDH/ER/KR1 | 2-desmethyl-3-deoxy-3-oxo | 14 | ND |

Figure 2A:
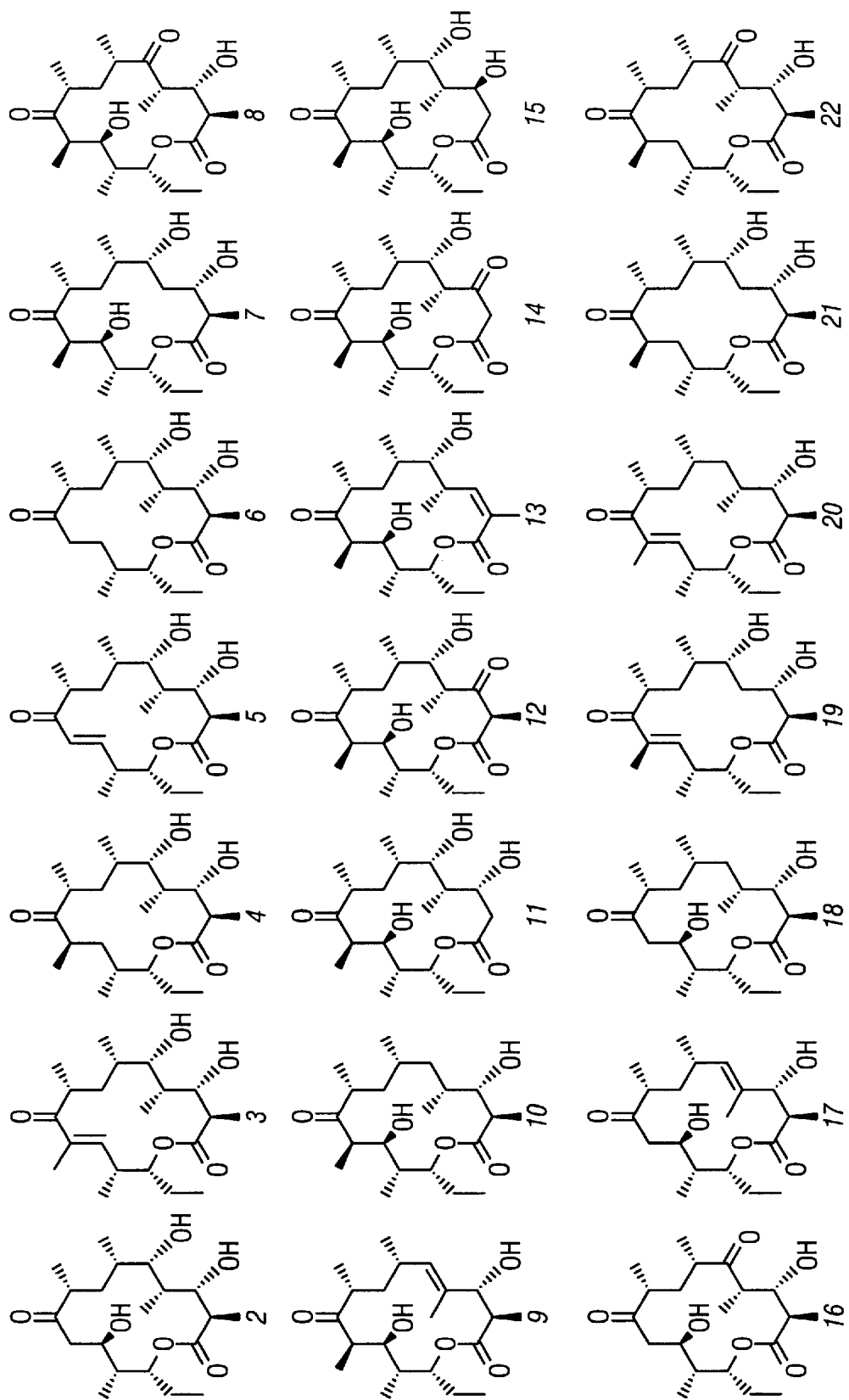
FIG. 2 shows the combinatorial library of erythronolide polyketides provided by the present invention.
Figure 2B:
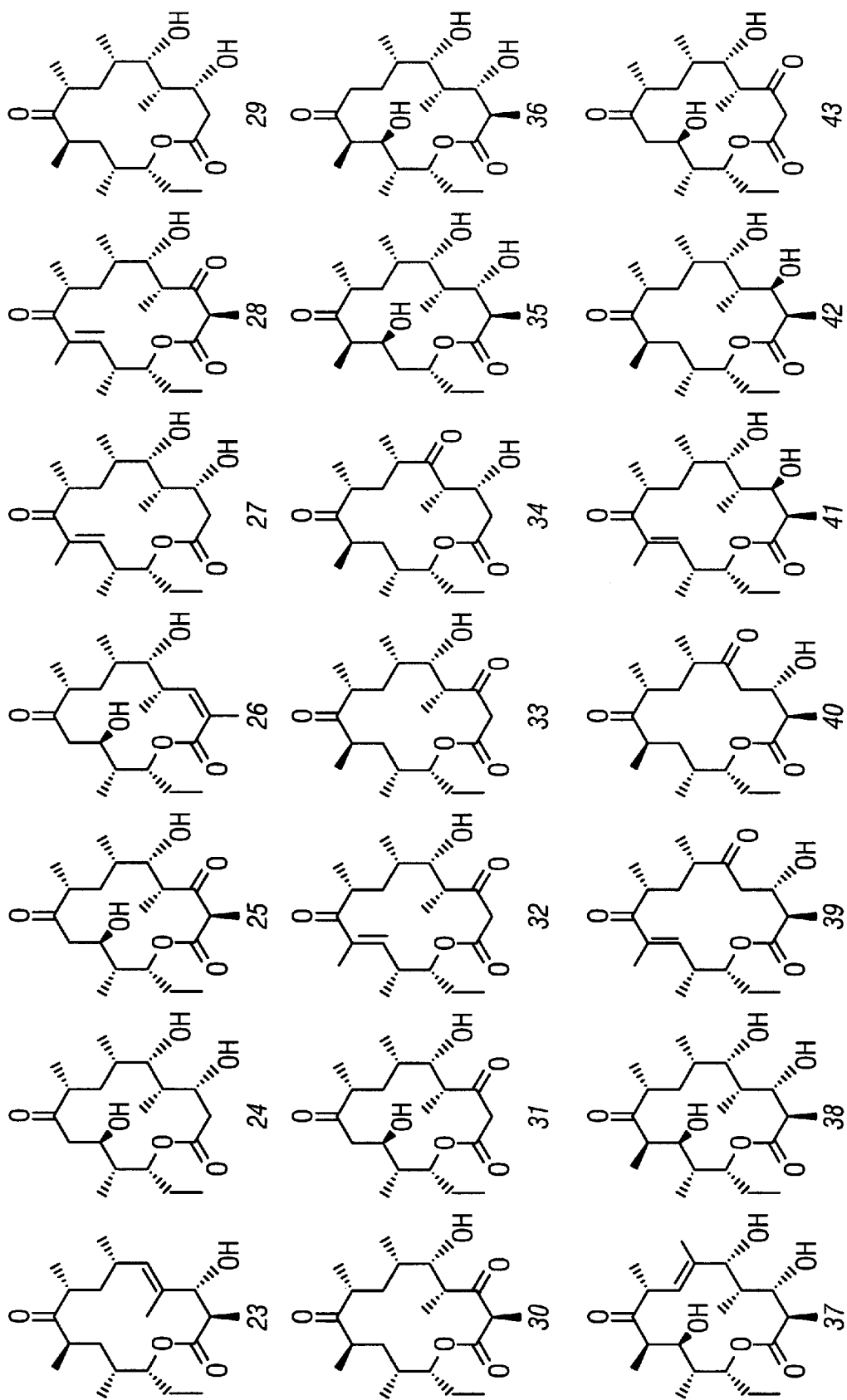
Figure 2C:
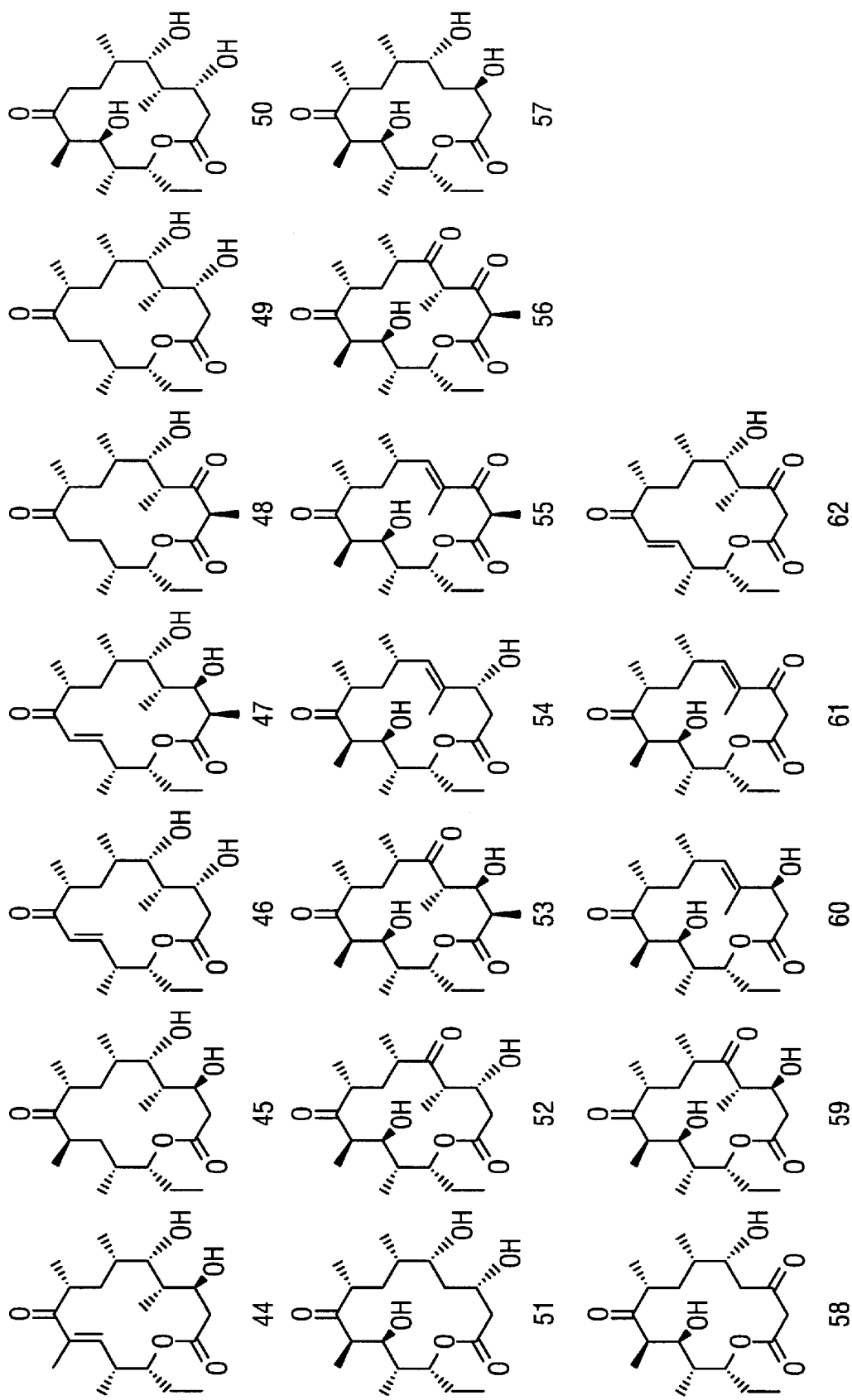

Yields are relative to 6-dEB (1) under similar conditions (~20 mg/L). Structures of compounds are shown in FIG. 2. ND is not determined.

The rapAT2 substitutions generated functional hybrid PKSs in each of the three modules, producing 10-desmethyl (2), 4-desmethyl (7), and 2-desmethyl (11) 6-dEB analogs as predicted. All three rapDH/KR4 substitutions also resulted in functional PKSs, generating 10,11-anhydro (3), 4,5-anhydro (9), and 2,3-anhydro (13) derivatives. The two strains carrying the AT/ACP linker substitutions in modules 5 and 6 produced 5-deoxy-5-oxo (8) (previously reported as erythromycins by Donadio et al., "Modular organization of genes required for complex polyketide biosynthesis," *Science* 252, 675–679 (1991)) from an eryKR5 deletion in *S. erythraea*), and 3-deoxy-3-oxo (12) 6-dEB analogs. However, a macrolide product was not detected from the PKS with the KR deletion in module 2, suggesting that either DEBS module 3 did not process the β-ketone triketide intermediate or the product was formed at low levels. Production of 11-deoxy (4) and 5-deoxy (10) 6-dEB analogs was achieved by replacing the existing KR in modules 2 or 5 with rapDH/ER/KR1. In addition, the C-3 ketone derivative, 8 (see above), was also produced with the rapDH/ER/KR1 replacement in module 5, suggesting that transfer of the unprocessed β-keto intermediate occurs at rates competitive with ketoreduction by rapKR1.

The rapDH/ER/KR1 substitution in module 6 failed to generate a fully C-3 reduced compound, and the observed ketone (12) and alkene (13) products suggested that reductions catalyzed by the KR and ER domains are slow relative to lactone formation by the TE. An unexpected macrolide product was also observed from the PKS with the AT/ACP linker substitution in module 6 (see Table 1, above). Purification and characterization by mass spectrometry and $^1$H and $^{13}$C-NMR spectroscopy revealed the structure to be 2-desmethyl-3-deoxy-3-oxo-6-dEB (14), which arises from misincorporation of an acetate monomer in module 6. Although relaxed specificities of AT domains are known (Stassi et al., "Ethyl-substituted erythromycin derivatives produced by directed metabolic engineering," *Proc. Natl. Acad. Sci. USA* 95, 7305–7309 (1998) and Kao et al., "Engineered biosynthesis of a complete macrolactone in a heterologous host," *Science* 265, 509–512 (1994)), it is not obvious how non-AT domain replacements can affect the specificity of monomer addition.

Next, substitution of both the AT and KR domains within a single module was performed in modules 2 and 6 to examine the tolerance for simultaneous alteration of extender unit and β-carbon processing within a single module. Six mutants were constructed, with three producing the targeted doubly modified 6-dEB analogs (see Table 1, above).

The absence of product from the PKS containing the rapAT2+AT/ACP linker double mutation in module 2 is consistent with the lack of product formation observed with the parental single AT/ACP linker substitution. The other two combinations in module 2, rapAT2+rapDH/KR4 and rapAT2+rapDH/ER/KR1, yielded small amounts of the expected 10-desmethyl-10,11-anhydro (5) and 10-desmethyl-11-deoxy (6) 6-dEB derivatives.

The PKS carrying the rapAT2+AT/ACP substitution in module 6 produced the anticipated 2-desmethyl-3-deoxy-3-oxo-6-dEB (14) with identical BPLC retention time and mass fragmentation pattern as the compound unexpectedly formed by the PKS with the AT/ACP substitution alone (see above). Compound 14 was also the only product identified with the module 6 rapAT2+rapDH/ER/KR1 combination and is consistent with the slow rate of ketoreduction observed for the single rapDH/ER/KR1 substitution at this position.

The rapAT2+rapDH/KR4 cassettes in module 6 produced a compound (14) with mass spectrum consistent with 2-desmethyl-6-dEB (11) indicating that ketoreduction, but not dehydration, occurred. However, because the rapKR4 domain catalyses ketoreduction with the opposite stereospecificity of eryKR6 (Kao et al., "Alcohol stereochemistry in polyketide backbones is controlled by the β-ketoreductase domains of modular polyketide synthases," *J. Am. Chem. Soc.* 120, 2478–2479 (1998)), and because the BPLC retention time of this compound is different from 11, 14 is determined to be the C-3 hydroxyl epimer of 11.

Substitutions in two separate modules were next engineered to manipulate biosynthetic steps more distant in the biosynthetic pathway. All functional single substitutions in module 2 were combined with all functional substitutions in module 5 or module 6, giving a total of sixteen combinations (see Table 2, below).

TABLE 2

Combinatorial double and triple substitutions and polyketide products

| | Mutation | | 6-dEB Analog | |
|---|---|---|---|---|
| | Module 2 | Module 5 or 6 | Product | Cmpd# |
| Module 2– Module 5 double mutants | rapAT2 | AT/ACP linker | 5-deoxy-5oxo-10-desmethyl | 16 |
| | rapAT2 | rapDH/KR4 | 4,5-anhydro-10-desmethyl | 17 |
| | rapAT2 | rapDH/ER/KR1 | 5-deoxy-5oxo-10-desmethyl; 5-deoxy-10-desmethyl | 16, 18 |
| | rapDH/KR4 | rapAT2 | 4-desmethyl-10,11-anhydro | 19 |

TABLE 2-continued

Combinatorial double and triple substitutions and polyketide products

| | Mutation | | 6-dEB Analog | |
|---|---|---|---|---|
| | Module 2 | Module 5 or 6 | Product | Cmpd# |
| | rapDH/KR4 | AT/ACP linker | 5-deoxy-5-oxo-10,11-anhydro | 20 |
| | rapDH/KR4 | rapDH/ER/KR1 | NP | |
| | rapDH/ER/KR1 | rapAT2 | 4-desmethyl-11-deoxy | 21 |
| | rapDH/ER/KR1 | AT/ACP linker | 5,11-dideoxy-5-oxo | 22 |
| | rapDH/ER/KR1 | rapDH/KR4 | 4,5-anhydro-11-deoxy | 23 |
| Module 2– Module 6 double mutants | rapAT2 | rapAT2 | 2,10-didesmethyl | 24 |
| | rapAT2 | AT/ACP linker | 3-deoxy-3-oxo-10-desmethyl | 25 |
| | rapAT2 | rapDH/KR4 | 2,3-anhydro-10-desmethyl | 26 |
| | rapDH/KR4 | rapAT2 | 2-desmethyl-10,11-anhydro | 27 |
| | rapDH/KR4 | AT/ACP linker | 3-deoxy-3-oxo-10,11-anhydro | 28 |
| | rapDH/ER/KR1 | rapAT2 | 2-desmethyl-11-deoxy | 29 |
| | rapDH/ER/KR1 | AT/ACP linker | 3-deoxy-3-oxo-11-deoxy | 30 |
| Module 2– Module 6 triple mutants | rapAT14 | rapAT2 + AT/ACP linker | 2,10-didesmethyl-3-deoxy-3-oxo | 31 |
| | rapDH/KR4 | rapAT2 + AT/ACP linker | 2-desmethyl-3-deoxy-3-oxo-10,11-anhydro | 32 |
| | rapDH/ER/KR1 | rapAT2 + AT/ACP linker | 2-desmethyl-3,11-dideoxy-3-oxo | 33 |
| Module 2– Module 5– Module 6 triple mutant | KR2-> rapDH/ER/KR1, | KR5->AT/ACP linker, AT6-> rapAT2 | 2-desmethyl-5,11-dideoxy-5-oxo | 34 |

Structures of polyketides are shown in FIG. 2. Compound yields from all the multiple mutants fell to below 0.1 mg/L and could not be accurately determined by ELSD, except compound 29, which was produced at approximately 0.2 mg/L.

Macrolide products were detected by LC/MS in the culture extracts from fifteen of these mutants, although production levels decreased compared to parental single domain replacements. In each case, the mass spectrum was consistent with the compound(s) expected from the newly introduced catalytic activities (compounds 16–30). The decline in polyketide titres by these combinatorial mutants probably reflects substrate preferences by downstream activities for distally altered regions of a biosynthetic intermediate.

Finally, triple domain substitutions were created to further test the catalytic pliancy of DEBS mutants. To optimize yields, only the most productive AT+KR double substitution in module 6 (rapAT2+AT/ACP linker) was combined with functional AT or KR substitutions in module 2 (rapAT2, rapDH/KR, rapDH/ER/KR1) (see Table 2, above). Analysis of the culture extracts indicated that these engineered DEBS produced compounds with mass spectra matching the expected 2,4-didesmethyl-3-deoxy-3-oxo (31), 2-desmethyl-3-deoxy-3-oxo-10,11-anhydro (32), and 2-desmethyl-3-10-dideoxy-3-oxo (33) 6-dEB macrolactones. A fourth triple mutant was also engineered, this time manipulating a catalytic domain in each of three modules. The most productive single substitutions from module 2 (rapDH/ER/KR1), module 5 (AT/ACP linker), and module 6

(rapAT2) were combined in a single DEBS construct (Table 2, above). Again, a compound was formed with mass spectra matching the expected analog, 2-desmethyl-5,11-dideoxy-5-oxo-6-dEB (34).

In addition to this series of combinatorial mutants, other substitutions have been successfully used to extend the number and diversity of compounds in the erythromycin library. These include replacement of the AT and KR domains in module 1 (with rapAT2 and rapKR2) to give the 12-nor-6-dEB analog (35) and module 3 (with rapAT2) to give the 8-nor-6-dEB analog (36), and of the DH/ER/KR domain in module 4 (with rapDH/KR4) to give the 6,7-anhydro-6-dEB analog (37). Substitution of the KR in module 6 with the KR from RAPS module 2, which catalyzes reduction with opposite stereospecificity to the DEBS KR, results in the formation of a 6-dEB analog with LC/MS consistent with an altered 3-hydroxyl stereochemistry (38).

The remainder of the compounds in FIG. 2 represent combinatorial substitutions in:

module 2 and module 5 (39, 40), including the rapDH/ER/KR1 substitution in module 2 and the rapAT2 and rap14 linker substitution in module 5 to yield the 4-nor-5-oxo-11-deoxy-6-dEB analog (40), module 2 and module 6 (41–49), including compound 43, which is identical to compound 31, above, module 3 and module 6 (50), and module 5 and module 6 (51–62), including the rapAT2 substitution in module 5 and the rapAT2 and rapKR2 substitution in module 6 to yield the 2,4-bisnor-3-oxo-6-dEB analog (58) as well as the 2,4-bisnor-3-epi-6-dEB analog, and the rapAT2 and rapDH/KR4 substitution in module 2 and the rapAT2 and rap14 linker substitutions in module 6 to yield the 2,10-bisnor-3-keto-10,11-anhydro-6-dEB analog (62).

This latter compound (62) shows that the present invention provides 6-dEB analogs produced by recombinant PKS genes comprising up to four different substitutions at levels detectable even in the small-scale cultures described in the Examples below. By using larger scale cultures, including large volume fermentors, one can produce any of the compounds of the invention, including compounds shown in the Tables above as not detected under the culture and assay conditions employed.

Moreover, the present invention provides novel polyketides produced by the combinatorial assembly of the recombinant PKS genes of the invention. Such combinatorial assembly includes the combination of a gene with one, two, or more changes, relative to the wild-type gene, with other genes that can include wild-type or recombinant genes. For example, the present invention provides a recombinant eryA1 gene that contains the rapAT2 domain substituted for the eryAT1 domain that produces a 12-nor-6-dEB analog when combined with wild-type eryAII and eryAIII genes. This recombinant eryAI gene can be combined with other mutant eryAII and/or eryAIII genes to provide additional polyketide compounds of the invention. Moreover, this recombinant eryAI gene can be further modified, for example, to change the KR domain of module 2, to provide another eryAI gene of the invention that can in turn be combined with wild-type and/or recombinant eryAII and eryAIII genes to provide additional polyketides of the invention.

The engineered DEBS reported here also produce detectable levels of one or more minor components, including the acetate starter unit analogs (producing the 13-C methyl derivative in addition to the 13-C ethyl derivatives shown in FIG. 2) of the major compounds (Kao et al., "Manipulation of macrolide ring size by directed mutagenesis of a modular polyketide synthase," *J. Am. Chem. Soc.* 117, 9105–9106 (1995) and Kao et al., "Engineered biosynthesis of a complete macrolactone in a heterologous host," *Science* 265, 509–512 (1994)). Taking these into account, over 100 novel macrolide products have been generated using a simple combinatorial set of a 6-module scaffold and 5 cassettes.

Additional diversity can be realized by combining the recombinant PKS genes of the invention with a gene that codes for a non-functional KS 1 domain and providing the PKS produced thereby with synthetic diketide compounds as described in PCT publication Nos. 99/03986 and 97/02358. The resulting polyketides contain substitutions at the C-13 other than ethyl (as shown in FIG. 2) and thus increase the diversity of the library of polyketides provided by the present invention.

Nature has exploited combinatorial biosynthesis to produce the library of some 7,000 polyketides that is currently known to man, of which about 150 are macrolide variants with about 30 different 12-, 14- and 16-macrolide ring structures (Kirst, H. A. (1992) in Kirk-Othmer Encyclopedia of Chemical Technology, ed. Howe-Grant, M. (Wiley, N.Y.), Vol. 3, pp. 169–213). However, the natural polyketides thus far revealed represent only a small fraction of the combinatorial potential that might be realized from permutations of modules in a PKS. For example, if the two AT and five beta-carbon modifier building blocks used here are permutated into the six modular DEBS PKS, the number of polyketides that would result is $10^7$; complete permutation of the 14-module RAPS PKS with the same building blocks could yield a remarkable $10^{14}$ polyketides! It seems reasonable to expect that the most interesting and important polyketides remain within the reservoir of yet undiscovered molecules.

While the library described herein that was created by engineering DEBS PKS falls far short of what is theoretically possible, the methods and reagents provided by the invention enables the creation of much larger libraries. Moreover, the number of polyketides described represents about 1% of the total polyketides known to man, and exceeds the total number of different macrolide ring structures yet discovered. Further, the structures described here have not been found in nature, so the present library is drawn from a yet unexplored pool of the potential polyketide library.

What is required to realize the combinatorial potential of polyketide diversity? The experiments described demonstrate manipulation of the major combinatorial elements that can be used for engineering modular polyketide biosynthetic pathways—AT substitution, KR deletion, KR gain-of-function and KR stereochemical alteration. Further, one or more of such modifications have been successfully applied to each of the six modules of DEBS, demonstrating a remarkable plasticity of the PKS towards foreign domains and intermediates. The present invention enables one to apply as many of these modifications to as many modules as possible successfully.

The present invention demonstrates that if two or more single PKS mutants are functional, it is likely that combinations of these will also produce the expected polyketide. The experiments described here reflect a stepwise approach of creating productive single mutants, then combining two or more of them to prepare multiple mutants. Given the six module DEBS, and the two ATs, and five beta-carbon modifier components described here, there are less than 60 possible single mutants to be prepared. Once a modest library of productive multiple mutants has been prepared, the introduction of additional productive mutations in the library results in a multiplicative increase in the library size. For example, introduction of 5 new mutations into each of two virgin modules of the library of 50 mutants would produce a library of 1150 polyketides, if all mutants were productive. With appropriate efforts, the present invention enables many or most single PKS mutants to be prepared to produce the expected polyketides.

Moreover, the present invention provides far more compounds than the erythronolides described in FIG. 2 or those that can be achieved by the methods described above. There are a wide variety of diverse organisms that can modify erythronolides such as those described here to provide compounds with or that can be readily modified to have useful activities. For example, *Saccharopolyspora erythraea* can convert 6-dEB to a variety of useful compounds. The erythronolide 6-dEB is converted by the eryF gene product to erythronolide B, which is, in turn, glycosylated by the eryB gene product to obtain 3-O-mycarosylerythronolide B, which contains L-mycarose at C-3. The enzyme eryC gene product then converts this compound to erythromycin D by glycosylation with D-desosamine at C-5. Erythromycin D, therefore, differs from 6-dEB through glycosylation and by the addition of a hydroxyl group at C-6. Erythromycin D can be converted to erythromycin B in a reaction catalyzed by the eryG gene product by methylating the L-mycarose residue at C-3. Erythromcyin D is converted to erythromycin C by the addition of a hydroxyl group at C-12 in a reaction catalyzed by the eryK gene product. Erythromycin A is obtained from erythromycin C by methylation of the mycarose residue in a reaction catalyzed by the eryG gene product.

The compounds provided by the present invention can be provided to cultures of *Saccharopolyspora erythraea* and converted to the corresponding derivatives of erythromycins A, B, C, and D in accordance with the procedure provided in Example 5, below. To ensure that only the desired compound is produced, one can use an *S. erythraea* eryA mutant that is unable to produce 6-dEB but can still carry out the desired conversions (Weber et al., 1985, *J Bacteriol.* 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production. Each of the erythromycins A, B, C, and D has antibiotic activity, although erythromycin A has the highest antibiotic activity. Moreover, each of these compounds can form, under treatment with mild acid, a C-6 to C-9 hemiketal with motilide activity. For formation of hemiketals with motilide activity, erythromycins B, C, and D, are preferred, as the presence of a C-12 hydroxyl allows the formation of an inactive compound that has a hemiketal formed between C-9 and C-12.

Thus, the present invention provides the compounds produced by hydroxylation and glycosylation of the compounds shown in FIG. 2 by action of the enzymes endogenous to *Saccharopolyspora erythraea* and mutant strains of *S. erythraea*. Such compounds are useful as antibiotics or as motilides directly or after chemical modification.

For use as antibiotics, the compounds of the invention can be used directly without further chemical modification. Erythromycins A, B, C, and D all have antibiotic activity, and the corresponding compounds of the invention that result from the compounds shown in FIG. 2 or the Example below being modified by *Saccharopolyspora erythraea* also have antibiotic activity. These compounds can be chemically modified, however, to provide other compounds of the invention with potent antibiotic activity. For example, alkylation of erythromycin at the C-6 hydroxyl can be used to produce potent antibiotics (clarithromycin is C-6-O-methyl), and other useful modifications are described in, for example, Griesgraber et al., 1996, *J. Antibiot.* 49: 465–477, Agouridas et al., 1998, *J Med. Chem.* 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; and 5,439,889; and PCT publication Nos. WO 98/09978 and 98/28316, each of which is incorporated herein by reference.

For use as motilides, the compounds of the invention can be used directly without further chemical modification. Erythromycin and certain erythromycin analogs are potent agonists of the motilin receptor that can be used clinically as prokinetic agents to induce phase III of migrating motor complexes, to increase esophageal peristalsis and LES pressure in patients with GERD, to accelerate gastric emptying in patients with gastric paresis, and to stimulate gall bladder contractions in patients after gallstone removal and in diabetics with autonomic neuropathy. See Omura et al., 1987, Macrolides with gastrointestinal motor stimulating activity, *J Med. Chem.* 30: 1941–3). The corresponding compounds of the invention that result from the compounds shown in FIG. 2 or the Example below being modified by *Saccharopolyspora erythraea* also have motilide activity, particularly after conversion, which can occur in vivo, to the C-6 to C-9 hemiketal by treatment with mild acid. Compounds lacking the C-12 hydroxyl are especially preferred for use as motilin agonists. These compounds can also be further chemically modified, however, to provide other compounds of the invention with potent motilide activity.

Moreover, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. Thus, *Streptomyces venezuelae*, which produces picromycin, contains enzymes that can transfer a desosaminyl group to the C-5 hydroxyl and a hydroxyl group to the C-12 position. In addition, *S. venezuelae* contains a glucosylation activity that glucosylates the 2'-hydroxyl group of the desosamine sugar. This latter modification reduces antibiotic activity, but the glucosyl residue is removed by enzymatic action prior to release from the cell. Another organism, *S. narbonensis*, contains the same modification enzymes as *S. venezuelae*, except the C-12 hydroxylase. Thus, the present invention provides the compounds produced by hydroxylation and glycosylation of the compounds shown in FIG. 2 by action of the enzymes endogenous to *S. narbonensis*, and *S. venezuelae*.

Other organisms suitable for making compounds of the invention include *Streptomyces antibioticus, Micromonospora megalomicea, S. fradiae*, and *S. thermotolerans. S. antibioticus* produces oleandomycin and contains enzymes that glycosylate the C-3 hydroxyl with oleandrose and the C-5 hydroxyl with desosamine, and an epoxidase that acts at C-8. *M megalomicea* produces megalomicin and contains enzymes that hydroxylates the C-6 and C-12 positions, glycosylates the C-3 hydroxyl with mycarose, the C-5 hydroxyl with desosamine, and the C-6 hydroxyl with megosamine (also known as rhodosamine), as well as acylating various positions. In addition to antibiotic activity, compounds of the invention produced by treatment with *M. megalomicea* enzymes can have antiparasitic activity as well. *S. fradiae* contains enzymes that glycosylate the C-5 hydroxyl with mycaminose and then the 4'-hydroxyl of mycaminose with mycarose, forming a disaccharide. *S. thermotolerans* contains the same activities as well as acylation activities. Thus, the present invention provides the compounds produced by hydroxylation and glycosylation of the compounds shown in FIG. 2 by action of the enzymes endogenous to *S. antibioticus, M. megalomicea, S. fradiae,* and *S. thermotolerans*.

The present invention also provides methods and genetic constructs for producing the glycosylated and/or hydroxylated compounds of the invention directly in the host cell of interest. Thus, the recombinant genes of the invention, which include recombinant eryAI, eryAII, and eryAIII genes with one or more deletions and/or insertions, including replacements of an eryA gene fragment with a gene fragment from a heterologous PKS gene, can be included on expression vectors suitable for expression of the encoded gene products in *Saccharopolyspora erythraea, Streptomyces antibioticus, Micromonospora megalomicea, S. fradiae,* and *S. thermotolerans*.

Moreover, additional recombinant gene products can be expressed in the host cell to improve production of a desired polyketide. As but one non-limiting example, certain of the recombinant PKS proteins of the invention produce a polyketide other than or in addition to the predicted Polyketide, because the Polyketide is cleaved from the PKS by the thioesterase (TE) domain in module 6 prior to processing by other domains on the PKS, in particular, the KR, DH, and/or ER domains in module 6. The production of the predicted polyketide can be increased in such instances by deleting the TE domain coding sequences from the gene and, optionally, expressing the TE domain as a separate protein. See Gokhale et al., Feb. 1999, "Mechanism and specificity of the terminal thioesterase domain from the erythromycin polyketide synthase," *Chem. & Biol.* 6: 117–125.

Many of the compounds of the invention contain one or more chiral centers, and all of the stereoisomers are included within the scope of the invention, as pure compounds as well as mixtures of stereoisomers. Thus the compounds of the invention may be supplied as a mixture of stereoisomers in any proportion.

The compounds of the invention can be produced by growing and fermenting the host cells of the invention under conditions known in the art for the production of other polyketides. The compounds of the invention can be isolated from the fermentation broths of these cultured cells and purified by standard procedures. The compounds can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138 or with a surfactant essentially as described in EPO patent publication No. 428,169.

Oral dosage forms may be prepared essentially as described by Hondo et al., 1987, *Transplantation Proceedings XIX*, Supp. 6: 17–22. Dosage forms for external application may be prepared essentially as described in EPO patent publication No. 423,714. The active compound is included in the pharmaceutical composition in an amount sufficient to produce the desired effect upon the disease process or condition.

For the treatment of conditions and diseases caused by infection, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

The compounds of the invention can be used as single therapeutic agents or in combination with other therapeutic agents. Drugs that can be usefully combined with compounds of the invention include one or more antibiotic or motilide agents.

A detailed description of the invention having been provided above, the following examples are given for the purpose of illustrating the invention and shall not be construed as being a limitation on the scope of the invention or claims. The following examples are given for the purpose of illustrating the present invention and shall not be construed as being a limitation on the scope of the invention or claims.

EXAMPLE 1

Restriction Site Engineering

PCR mutagenesis was used to introduce restriction sites in subclones containing portions of the DEBS genes. Replacement of the DEBS domains by the RAPS cassettes were performed in the subclones before introduction into pCK7 (Kao et al., "Engineered biosynthesis of a complete macrolactone in a heterologous host," Science 265, 509–512 (1994)) or pKOS011-77, which contains a kanamycin resistance-conferring gene and an additional restriction enzyme recognition site, described below, in the eryAI gene. The PstI and XbaI sites in module 2 are identical to those previously reported (Bedford et al., "A functional chimeric modular polyketide synthase generated via domain replacement," Chem. & Biol 3, 827–831 (1996)). The remaining engineered sites generated the following sequences at the domain boundaries (restriction sites underlined):

module 1 BamHI, GGCGCAGCAG GGATCCGTCTTCGTCT, (SEQ ID NO:1)

module 1 PstI, GCGCGTCTGG CTGCAGCCGAAGCCGG, (SEQ ID NO:2)

module 1 XbaI, GCCGGCCGAA TCTAGAGTGGGCGCGC, (SEQ ID NO:3)

module 2 BamHI, TCCGACGGT GGATCCGTGTTCGTC, (SEQ ID NO:4)

module 3 BanHi, GGACGGGCGC GGATCCGTCTTCCTGT, (SEQ ID NO:5)

module 3 PstI, GCGCTACTGG CTGCAGCCCGCCGCAC, (SEQ ID NO:6)

module 3 XbaI, GACCGGCGAG TCTAGACAACGGCTCG, (SEQ ID NO:7)

module 4 BamHI, CGCGCCGCGC GGATCCGTCCTGGTCT, (SEQ ID NO:8)

module 4 PstI, GCGCTTCTGG CTGCAGCCGCACCGGC, (SEQ ID NO:9)

module 4 XbaI, AGGGCCGAAC TCTAGAGACCGGCTCG, (SEQ ID NO:10)

module 5 BamHI, ACTCGCCGC GGATCCGCGATGGTG, (SEQ ID NO:11)

module 5 PstI, CGGTACTGGCTGCAGATCCCCACC, (SEQ ID NO:12)

module 5 XbaI, GAGGAGGGC TCTAGACTCGCCCAG, (SEQ ID NO:13)

module 6 BamHI, TCCGCCGGC GGATTCGTTTTCGTC, (SEQ ID NO:14)

module 6 PstI, CGGTACTGGCTGCAGCCGGAGGTG, and (SEQ ID NO:15)

module 6 XbaI, GTGGGGGCCTCTAGAGCGGTGCAG (SEQ ID NO:16).

In addition to the foregoing, an SpeI site was engineered in plasmid pKOS011-77 downstream of the ACP2 domain with the following oligonucleotide: CGGTTTCCTC ACTAGTGAGCTCGGCA (SEQ ID NO:17).

EXAMPLE 2

Construction of Replacement Cassettes

Construction of the rapDH/KR4 and rapDH/ER/KR1 cassettes was previously described (McDaniel et al., "Gain-of-function mutagenesis of a modular polyketide synthase," J. Am. Chem. Soc. 119, 4309–4310 (1997) and Kao et al., "Gain of function mutagenesis of the erythromycin polyketide synthase. 2. Engineered biosynthesis of an eight-membered ring tetraketide lactone," J. Am. Chem. Soc. 119, 11339–11340 (1997)). Oligonucleotide primers used for PCR amplification of rapAT2 are:

forward, 5'-TTT GGATCCGTGTTCGTCTTCCCGGGTCAG GGGTCG-3';

reverse, 5'-TTT CTGCAGCCAGTACCGCTGGTGCTGGAAG GCGTA-3'.

The underlined residues indicate the BamHI and PstI sites that can be used for ligation to the engineered DEBS sites. The AT/ACP linker was generated by annealing the following two oligonucleotides which create cohesive ends for ligation to the PstI and XbaI sites in DEBS (both shown in the 5'-3' orientation):

forward: CCGGTGCGGCTCGACGGAGAATTCGCG- CATCATCATCATCATCATTAACTGC A; reverse: GTTAATGATGATGATGATGATGCGC- GAATTCTCCGTCGAGCCGCA. The sequence contains portions of ery DNA between the AT and KR, and the KR and ACP domains of DEBS module 2.

EXAMPLE 3

Production and Analysis of Polyketides

S. coelicolor CH999 and S. lividans K4-114 are genetically engineered strains containing chromosomal deletions of the entire ca. 22 kb actinorhodin polyketide gene cluster (McDaniel et al., "Engineered biosynthesis of novel polyketides," Science 262, 1546–1557 (1993)). Macrolide production from DEBS is indistinguishable when expressed in either host strain under the conditions described. Strains expressing the mutant PKSs were grown as confluent lawns on R2YE agar medium (Hopwood et al., "Genetic manipulation of Streptomyces: A laboratory manual" (The John Innes Foundation, Norwich, 1985)) supplemented with 5 mM sodium propionate. The petri plates (13×150 mm) were fitted with sterile filter disks (Whatman no. 52, 125 mm) before filling with 50 mL of media. After 3 days growth, the filter paper and agar were transferred to another petri dish containing 50 mL of liquid R2YE (plus 5 mM sodium propionate), XAD-16 resin, and 6 mm glass beads for support. After 5 additional days growth, the XAD resin was collected and extracted with 10 mL of ethanol. The ethanol extracts were dried and partitioned between ethyl acetate and saturated aqueous $NaHCO_3$. The ethyl acetate fractions were analyzed by HPLC (C-18 column, water-acetonitrile gradient) coupled to APCI/MS. Quantitative determination of polyketides was made with evaporative light scattering detection (ELSD). Compounds identified here are the major metabolites produced. Some strains also contained detectable levels of one or more minor components.

EXAMPLE 4

Characterization of Compounds

Structure determination was primarily based on the agreement between the structure predicted for the directed mutagenesis performed and the mass spectrum. Under the chemical ionization conditions used for mass spectrometry, 6-dEB and its analogs generate signature dehydration patterns corresponding to the ring hydroxyls and lactone group. Compound 11 was previously reported by Liu et al. who engineered a similar DEBS mutant (Liu et al., "Biosynthesis of 2-nor-6-deoxyerythronolide B by rationally designed domain substitution," J. Am. Chem. Soc. 119, 10553–10554 (1997)).

EXAMPLE 5

Recombinant Constructs and Erythronolides

While the genetic constructs used to produce the compounds in FIG. 2 have been described above, the present invention provides a variety of different compounds for certain compounds of the invention as described below. Various additional compounds of the invention and the genetic constructs that can be used to prepare these compounds of the invention are also described in tabular form below.

DEBS KR DOMAIN SWAPS

Cassettes:

| | | | | | |
|---|---|---|---|---|---|
| •eryKR5 | KOS001-39 | •rapDH/ER/KR1 | KOS008-38 | •rapDH/ER/KR7 | |
| | KOS014-59 | | | | |
| •eryKR6 | KOS001-44 | •rapKR2 | KOS008-36 | •rapDH/KR9 | |
| | KOS014-35 | | | | |
| •eryDH/ER/KR4 | KOS007-29 | •rapKR4 | KOS008-37 | •rapDH/KR10 | |
| | KOS014-47 | | | | |
| •rapDH/KR4 | KOS001-62 | •rapDH/ER/KR13 | KOS014-57 | •rapDH/KR6(nf) | |
| | KOS014-2 | | | | |
| •rap 14 linker | KOS005-16dup | | | | |

KR2, DEBSmod1,2,3,4,5,6

```
           1               2           3           4           5           6
|-----------------•------|-----|->--------------•----------------->-----------------•------
-------->
                          KR2
```

| | in puc (Pac/Xba) | in expression (KAO127) | product |
|---|---|---|---|
| rapDH/ER/KR1 | KAO409 | KOS011-66 | 11-deoxy-6dEB |
| rapDH/KR4 | KOS009-7 | KOS011-64 | 10, 11-anhydro-6dEB |
| | in puc (Pac/Spe) | in expression (11–77) | product |
| rapDH/KR4 | KOS015-56 | KOS015-71 | 10, 11-anhydro-6dEB |
| rapDH/KR9 | ... | KOS015-101 | 10, 11 anhydro-6dEB* |
| rapDH/ER/KR1 | KOS015-57 | KOS015-72 | 11-deoxy-6dEB/10, 11-anhydro-6dEB |
| rapDH/ER/KR13 | KOS014-63 | KOS023-13 | 11-deoxy-6dEB |

KR3, DEBSmod1,2,3,4,5,6

```
           1               2           3           4           5           6
|-----------------•------------->--------|---|---•----------------->-----------------•------
-------->
                              KR3
```

| | in puc (Spe/Bgl) | in expression (11–77) | product |
|---|---|---|---|
| rapmod14 linker | KOS024-22 | KOS024-32 | 6-dEB |
| rapKR2 | KOS024-23 | KOS024-33 | 6-dEB |
| rapDH/KR4 | KOS024-24 | KOS024-34 | 6-dEB |

DH/ER/KR4, DEBSmod1,2,3,4,5,6

```
           1               2           3           4           5           6
|-----------------•------------->-----------------•---------|---|----->-----------------•------
-------->
                                          DH/ER/KR4
```

| | in delivery vector | in expression | product |
|---|---|---|---|
| eryDH/ER/KR4 | KOS008-16 | KOS011-4 | 6-dEB |
| rapDH/ER/KR1 | KOS008-42 | KOS011-19 | 6-epi-6-dEB |
| rapDH/KR4 | KOS008-44 | KOS011-21 | 6,7-anhydro-6-dEB |
| rapmod14 linker | KOS008-45 | KOS011-22 | 7-keto-6dEB |

-continued

DEBS KR DOMAIN SWAPS

KR5, DEBSmod1,2,3,4,5,6

```
       1              2              3              4              5         6
|---------------•-------------> •-----------------•----------------> -----|---|--------•-----
--------->                                                  KR5
```

|  | in puc (Bgl/RI) | in expression (KAO127) | product |
|---|---|---|---|
| eryKR5 | KOS006-182 | KOS016-29 | 6-dEB |
| rapmod14 linker | KOS016-12 | KOS016-28 | 5-keto-6dEB |
| rapKR4 | ... | KOS016-148b | 5-keto-6dEB |
| rapDH/KR4 | KOS006-178 | KOS016-32 | 4,5-anhydro-6dEB |
| rapDH/ER/KR1 | KOS006-176 | KOS026-18b | 5-deoxy-6dEB |
| rapDH/ER/KR7 | KOS023-1 | KOS023-8 | 5-keto-6dEB |
| rapDH/ER/KR13 | KOS023-3 | KOS023-10 | 5-deoxy-6dEB |

KR6, DEBSmod1,2,3,4,5,6

```
       1              2              3              4              5         6
|---------------•--------------> •----------------•---------------->-------------•-----
-•--|---|-->
```

|  | in delivery vector | in expression | product |
|---|---|---|---|
| eryKR6 | KOS008-49 | KOS011-26 | 6-dEB |
| rapmod14 linker | KOS011-12 spiroketals | KOS011-13 | 3-keto-6dEB, 2-nor-3-keto-6dEB, spiroketals |
| ΔKR6 |  | KOS024-9 | 3-keto-6dEB, 2-nor-3-keto-6dEB, spiroketals |
| rapKR2 | KOS011-69 | KOS011-74 | 3-epi-6dEB, 3-keto products |
| rapKR4 | KOS011-70 | KOS011-75 | 3-epi-6dEB |
| rapDH/KR4 | KOS008-48 | KOS011-25 | 2,3-anhydro-6dEB |
| rapDH/ER/KR1 | KOS008-46 | KOS011-23 | 2,3-anhydro-6dEB, 3-keto products |

DEBS AT DOMAIN SWAPS

Cassettes:

| •eryAT4 (propionate) | KOS003-1 | •rapAT2 (acetate) | KOS008-50 |
|---|---|---|---|
| •rapAT4 (propionate) | KOS011-30 |  |  |
| rapAT5 (acetate) | KOS016-X | •rapAT14 (acetate) | KOS014-30 |

AT1, DEBSmod1,2,3,4,5,6

```
       1              2              3              4              5         6
|--|-----|----------•------------------> -----------•-------------> ----------•-----
-•------->          AT1
```

|  | in puc (Pac/Xba) | in expression | product |
|---|---|---|---|
| rapAT2* | KOS011-38 | KOS024-15 | 12-nor-6dEB |

* also contains rapKR2 in module1

| DEBS AT + KR DOMAIN SWAPS | | | |
|---|---|---|---|
| AT | KR | construct | product |
| DEBS Module 2 | | | |
| rapAT2 | rapKR2 | KOS015-82 | 2-nor-3-epi-TKL |
| rapAT2 | rapDH/KR4 | KOS015-83 | 10-nor-10,11-anhydro-6dEB |
| rapAT2 | rapDH/ER/KR1 | KOS015-84 | 10-nor-11-deoxy-6dEB* |
| DEBS Module 5 | | | |
| rapAT2 | rap 14 linker | KOS016-100 | 4-nor-5-keto-6dEB* |
| DEBS Module 6 | | | |
| rapAT2 | rapKR2 | KOS015-106 | 2-nor-3-epi-6dEB |
| rapAT2 | rapDH/KR4 | KOS015-107 | 2-nor-3-epi-6dEB |
| rapAT2 | rapDH/ER/KR1 | KOS015-108 | 2-nor-3-keto-6dEB |
| rapAT2 | rap 14 linker | KOS015-109 | 2-nor-3-keto 6dEB |
| rapAT2 | rapDH/KR9 | KOS015-154 | 2-nor-2,3-anhydro-6dEB |

| DEBS MUTANT CROSSES | | | | | |
|---|---|---|---|---|---|
| DEBS Module 2 × Module 5 | | | | | |
| AT2 | KR2 | AT5 | KR5 | construct | product |
| rapAT2 | | | rap14linker | KOS011-84 | 5-keto-10-nor-6dEB* |
| rapAT2 | | | rapDH/KR4 | KOS011-90 | 4,5-anhydro-10-nor-6dEB* |
| rapAT2 | | | rapDH/ER/KR1 | KOS024-70 | 5-deoxy-10-nor-6dEB + 5-keto-10-nor-6dEB |
| | rapDH/KR4 | rapAT2 | | KOS011-82 | 4-nor-10,11-anhydro-6dEB* |
| | rapDH/KR4 | | rap14linker | KOS011-85 | 5-keto-10,11-anhydro-6dEB* |
| | rapDH/KR4 | | rapDH/KR10 | KOS011-96 | 5-keto-10,11-anhydro-6dEB* |
| | rapDH/ER/KR1 | rapAT2 | | KOS011-83 | 4-nor-11-deoxy-6dEB + dehydrated* |
| | rapDH/ER/KR1 | | rap14linker | KOS011-86 | 5-keto-11-deoxy-6dEB |
| | rapDH/ER/KR1 | | rapDH/KR4 | KOS011-91 | 4,5-anhydro-11-deoxy-6dEB* |
| | rapDH/KR4 | rapAT2 | rap14linker | KOS011-87 | 4-nor-5-keto-10,11-anhydro-6dEB* |
| | rapDH/ER/KR1 | rapAT2 | rap14linker | KOS011-88 | 4-nor-5-keto-11-deoxy-6dEB* |
| DEBS Module 2 × Module 6 | | | | | |
| AT2 | KR2 | AT6 | KR6 | construct | product |
| rapAT2 | | rapAT2 | | KOS015-116 | 2,10-didesmethyl-6dEB |

| DEBS MUTANT CROSSES | | | | |
|---|---|---|---|---|
| rapAT2 | | rap14linker | KOS015-41 | 3-keto-10-nor-6dEB + 10-nor-spiroketal* |
| rapAT2 | | rapKR2 | KOS015-87 | 3-keto-10-nor-6dEB |
| rapAT2 | | rapDH/KR4 | KOS015-40 | 2,3-anhydro-10-nor-6dEB |
| rapDH/KR4 | rapAT2 | | KOS015-42 | 2-nor-10,11-anhydro-6dEB |
| rapDH/KR4 | | rap14linker | KOS015-43 | 3-keto-10,11-anhydro-6dEB* |
| rapDH/KR4 | | rapKR2 | KOS015-88 | 3-epi-10,11-anhydro-6dEB and 3-keto* |
| rapDH/ER/KR1 | rapAT2 | | KOS015-44 | 2-nor-11-deoxy-6dEB |
| rapDH/ER/KR1 | | rap14linker | KOS015-46 | 3-keto-11-deoxy-6dEB |
| rapDH/ER/KR1 | | rapKR2 | KOS015-89 | 3-epi-11-deoxy-6dEB and 3-keto product* |
| rapDH/ER/KR1 | | rapDH/KR4 | KOS015-45 | 2,3-anhydro-11-deoxy-6dEB |
| rapAT14 | | rapAT2 | KOS015-117 | 2,10-didesmethyl-6dEB |
| rapAT14 | | rapAT2 rap14linker | KOS015-120 | 2,10-didesmethyl-3-keto-6dEB and spiroketal* |
| rapAT14 | | rapAT2 rapKR2 | KOS015-118 | 2,10-didesmethyl-3-keto-6dEB and spiroketal* |
| rapAT14 | | rapAT2 rapDH/KR4 | KOS015-119 | 2,10-didesmethyl-3-keto-6dEB and spiroketal* |
| rapDH/KR4 | rapAT2 | rap14linker | KOS015-122 | 2-nor-3-keto-10,11-anhydro-6dEB* |
| rapDH/KR4 | rapAT2 | rapKR2 | KOS015-121 | 2-nor-3-epi-10,11-anhydro-6dEB* |
| rapDH/ER/KR1 | rapAT2 | rap14linker | KOS015-125 | 2-nor-3-keto-11-deoxy-6dEB |
| rapDH/ER/KR1 | rapAT2 | rapKR2 | KOS015-123 | 2-nor-3-epi-11-deoxy-6dEB |
| rapDH/ER/KR1 | rapAT2 | rapDH/KR4 | KOS015-124 | 2-nor-3-epi-11-deoxy-6dEB |
| rapAT2 | rapDH/KR4 | rapAT2 | KOS015-150 | 2,10-didesmethyl-10,11-anhydro-6dEB* |
| rapAT2 | rapDH/KR4 | rapKR2 | KOS015-127 | 3-epi-10-nor-10,11-anhydro-6dEB |

-continued

DEBS MUTANT CROSSES

| rapAT2 | rapDH/ KR4 | rapAT2 | rap14linker | KOS015-152 | 2,10-didesmethyl-3keto-10,11-anhydro-6dEB |
|---|---|---|---|---|---|
| rapAT2 | rapDH/ ER/ KR1 | | rap14linker | KOS015-158 | 3-keto-10-nor-11-deoxy-6dEB* |
| rapAT2 | rapDH/ ER/ KR1 | rapAT2 | | KOS015-159 | 2,10-didesmethyl-11-deoxy-6dEB* |

DEBS Module 5 × Module 6

| AT5 | KR5 | AT6 | KR6 | construct | product |
|---|---|---|---|---|---|
| rapAT2 | | rapAT2 | | KOS016-183f | 2,4-didesmethyl-6dEB* |
| | rap14-linker | rapAT2 | | KOS016-152k | 2-nor-5-keto-6dEB |
| | rap14-linker | | rapKR4 | KOS016-150b | 3-epi-5-keto-6dEB* |
| | rapDH/ KR4 | rapAT2 | | KOS016-152e | 2-nor-4,5-anhydro-6dEB and 2-nor-5-keto-6dEB |
| | rapDH/ KR4 | | rap14linker | KOS016-133k | 3-keto-4,5-anhydro-6dEB and 3,5-dioxo-6dEB* |
| | rapDH/ KR4 | | rapKR2 | KOS016-133b | 3-keto-4,5-anhydro-6dEB and 3,5-dioxo-6dEB* |
| | rapDH/ KR4 | | rapKR4 | KOS016-148e | 3-keto-4,5-anhydro-6dEB and 3,5-dioxo-6dEB* |
| rapAT2 | | rapAT2 | rapKR2 | KOS016-183g | 2,4-didesmethyl-3-epi-6dEB* |
| | rap14-linker | rapAT2 | rapKR2 | KOS016-152i | 2-nor-3-epi-5-keto-6dEB* |
| | rapDH/ KR4 | rapAT2 | rapKR2 | KOS016-152f | 2-nor-3-epi-4,5-anhydro-6dEB and 3-keto* 2-nor-3-keto-4,5-anhydro-6dEB and hemiketal |
| | rapDH/ KR4 | rapAT2 | rap14linker | KOS016-152g | 6dEB and 3-keto* 2-nor-3-keto-4,5-anhydro-6dEB and hemiketal |
| mod3 | | mod6 | | construct | product |
| rapAT2 | | rapAT2 | | KOS015-34 | 2,8-didesmethyl-6dEB |
| mod2 | mod5 | mod6 | | construct | product |
| rapDH/ ER/KR1 | rap14-linker | rapAT2 | | KOS015-162 | 2-nor-5-keto-11-deoxy-6dEB |

*produce at <0.1 mg/L

EXAMPLE 6

Conversion of Erythronolides to Erythromycins

A sample of an erythronolide (~50 to 100 mg) is dissolved in 0.6 mL of ethanol and diluted to 3 mL with sterile water. This solution is used to overlay a three day old culture of *Saccharopolyspora erythraea* WHM34 (an eryA mutant) grown on a 100 mm R2YE agar plate at 30° C. After drying, the plate is incubated at 30° C. for four days. The agar is chopped and then extracted three times with 100 mL portions of 1% triethylamine in ethyl acetate. The extracts are combined and evaporated. The crude product is purified by preparative HPLC (C18 reversed phase, water-acetonitrile gradient containing 1% acetic acid). Fractions are analyzed by mass spectrometry, and those containing pure compound are pooled, neutralized with triethylamine, and evaporated to a syrup. The syrup is dissolved in water and extracted three times with equal volumes of ethyl acetate. The organic extracts are combined, washed once with saturated aqueous $NaHCO_3$, dried over $Na_2SO_4$, filtered, and evaporated to yield ~0.15 mg of product.

All references cited herein are incorporated herein by reference. The invention having now been described by way of written description and examples, those of skill in the art will recognize that the invention can be practiced in a variety of embodiments and that the foregoing description and examples are for purposes of illustration and not limitation of the following claims.

We claim:

1. A polyketide selected from the group consisting of 5,6-dideoxy-10-norerythronolide B, 2,10-bisnor-3-oxo-6-deoxy-10,11-anhydroerythronolide B, and 2,4-bisnor-3-oxo-6-deoxyerythronolide B, and the glycosylated and hydroxylated forms thereof, in substantially pure form.

2. The polyketide of claim 1 that is 5,6-dideoxy-10-norerythronolide B.

3. The polyketide of claim 1 that is 2,10-bisnor-3-oxo-6-deoxy-10,11-anhydroerythronolide B.

4. The polyketide of claim 1 that is 2,4-bisnor-3-oxo-6-deoxy erythronolide B.

* * * * *